(12) United States Patent
Beffy et al.

(10) Patent No.: US 6,202,489 B1
(45) Date of Patent: Mar. 20, 2001

(54) ULTRASONIC TESTING METHOD FOR A PART OF COMPLEX GEOMETRY

(75) Inventors: Lionel Beffy, Courcouronnes; Mathias Alexandre Fink, Meudon; Yves Gérard Mangenet, Epinay Sous Senart; Véronique Miette, Paris; Jean François Wu, Orsay, all of (FR)

(73) Assignee: Societe Nationale d'Etude et de Construction de Moteurs d'Aviation (S.N.E.C.M.A.) (FR)

( * ) Notice: Subject to any disclaimer, the term of this patent is extended or adjusted under 35 U.S.C. 154(b) by 0 days.

(21) Appl. No.: 09/302,374

(22) Filed: Apr. 30, 1999

(30) Foreign Application Priority Data

May 7, 1998 (FR) .................................................. 98 05776

(51) Int. Cl.[7] .......................... G01N 29/04; G01N 29/10
(52) U.S. Cl. .................................. 73/628; 73/641; 73/622
(58) Field of Search .............................. 73/641, 642, 644, 73/620, 622, 625, 626, 627, 628, 618, 637, 602, 606

(56) References Cited

U.S. PATENT DOCUMENTS

| | | | |
|---|---|---|---|
| 4,604,897 | * | 8/1986 | Saglio ..................................... 73/641 |
| 5,457,996 | | 10/1995 | Kondo et al. . |
| 5,513,532 | * | 5/1996 | Beffy et al. ............................... 73/641 |
| 5,533,401 | * | 7/1996 | Gilmore ................................... 73/641 |
| 5,677,491 | * | 10/1997 | Ishrak et al. ............................. 73/641 |
| 5,798,461 | * | 8/1998 | Banta, Jr. et al. ....................... 73/641 |

FOREIGN PATENT DOCUMENTS

| | | |
|---|---|---|
| 0 480 086 A1 | 4/1992 | (EP) . |
| 0 598 661 A1 | 5/1994 | (EP) . |
| WO96/24053 | 8/1996 | (JP) . |

* cited by examiner

Primary Examiner—Helen Kwok
(74) Attorney, Agent, or Firm—Bacon & Thomas PLLC

(57) ABSTRACT

An ultrasonic testing method for parts of complex geometry comprises using a multielement transducer transmitting focused ultrasonic waves into the part to be tested. The focusing of the ultrasonic waves is implemented in two different modes using multichannel control electronics. The two focusing modes are an electronic focusing mode and a time reversal focusing mode which are selected as a function of the depth of the particular test zone. The time reversal focusing mode is selected to test central zones located at the largest depths around the longitudinal axis of the part. The electronic focusing mode is selected to test intermediate zones situated at depths between the central zones and a peripheral zone of the part.

9 Claims, 5 Drawing Sheets

ULTRASONIC TESTING METHOD FOR A PART OF COMPLEX GEOMETRY

BACKGROUND OF THE INVENTION

1. Field of the Invention

The invention relates to an ultrasonic testing method, particularly of an immersed, cylindrical part. More specifically, the invention relates to such a method for detecting internal defects within billets such as titanium billets used in aeronautics.

2. Description of the Related Art

Many part testing systems which operate in the ultrasonic transmission or reflection mode are known.

Ultrasonic part testing may be implemented using a plurality of acoustic transducers elements of fixed focus to detect defects at different depths in the part being tested. Each transducer emits an ultrasonic beam focused at a predetermined depth in the part. The transducers are fitted with focal planes at increasing depths to allow testing the entire volume of the part from the surface to the center.

Ultrasonic part testing also may be carried out using an acoustic probe comprising several electronically focused transducer elements, in which the focusing is implemented by applying different time delays to the signals emitted by each transducer. When obtaining a part's image and using a grid of transducers as the source/receiver, a major difficulty is encountered in that echoes from the reflection at the microstructure of the material are high relative to echoes from any defects such that the former echoes mask the latter. This problem is compounded when the shape of the part is complex and/or the part has a heterogeneous structure, for instance in the case of titanium billets.

It is known to overcome this problem using an appropriate ultrasonic amplification technique with conjugate phase, also called time reversal. According to this technique, following transmission of an unfocused or barely focused ultrasonic beam and reception of the echo returned by the defect to be detected, the returned echo is re-emitted after its time and shape distribution have been reversed in time. An application of this procedure to ultrasonic, cylindrical part testing is described in U.S. Pat. No. 5,513,532. This technique allows optimal focusing on any defect in heterogeneously structured parts such as titanium parts; however, it suffers the major drawback of being time-consuming in the focusing of the ultrasonic beam, thereby substantially increasing the time required to inspect the part as compared to the conventional procedures using electronic focusing.

SUMMARY OF THE INVENTION

The objective of the invention is to mitigate the drawbacks of the known ultrasonic tests for parts of complex geometry and heterogeneous structure such as titanium billets, such that the testing of the part's volume is accomplished in a minimum of time and with a constant and highest possible detection sensitivity level.

To that end, the testing method according to the invention uses a multi-element transducer transmitting focused ultrasonic waves into the part, with the focusing being carried out in two different modes by multichannel electronics. The two focusing modes are an electronic focusing mode and a time reversal focusing mode, which are selected as a function of the depth of the zone being tested.

The time reversal focusing mode is selected to inspect central zones located at the largest depths around the longitudinal axis of the part.

The electronic focusing mode is selected to inspect intermediate zones located at depths between the central zones and a peripheral zone of the part.

According to the invention, ultrasonic immersion testing of a geometrically complex part having a longitudinal axis is carried out such that during rotation of the part, ultrasonic waves are transmitted into test zones located at different billet depths, with the focusing being carried out by one transducer, comprising a plurality of transducing elements, in two different focusing modes, which are selected as a function of the depth of the particular zone being tested.

BRIEF DESCRIPTION OF THE DRAWINGS

Other features and advantages of the invention are elucidated below in an illustrative and non-limiting description of preferred embodiments, with reference to the attached drawings, in which.

DETAILED DESCRIPTION OF THE PREFERRED EMBODIMENTS

Figure 1:
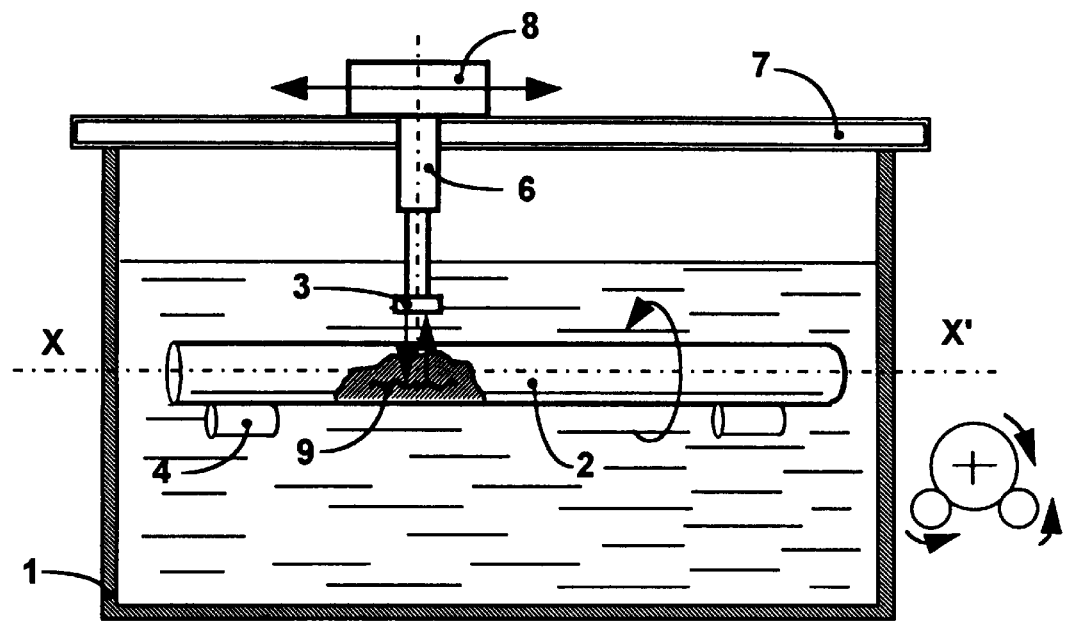
FIG. 1 is a simplified longitudinal section of an ultrasonic testing apparatus according to the invention.

FIG. 1 is a longitudinal section of an ultrasonic testing apparatus according to the invention for a body of revolution, for instance a titanium billet.

This apparatus comprises a tub 1 filled with an acoustically coupling medium which is kept at a fixed level, for example by an overflow device (omitted). For the sake of simplification, the filling and draining ducts are omitted as well. A part 2 to be tested and an ultrasonic transducer 3 are immersed inside the tub 1. Rotational drive rollers 4 assure rigorous centering of the part 2 on its axis XX'. The transducer 3 is rigorously kept perpendicular to the axis XX' by a support 6 which is adjustable, in particular with respect to height. Moreover, in a known manner, the apparatus is fitted with means (omitted) to drive the part 2 into rotation at a specified angular speed and with means 7, 8 to longitudinally displace the transducer.

The transducer 3 is a multielement transceiver comprising piezoelectric pellets arrayed in matrix as described further below.

Use of the immersion tub 1 offers many advantages. In particular, it eliminates contact between the transducer 3 and the part 2 being tested, coupling being assured by water, optionally containing wetting agents such as oil. However, total immersion is not mandatory within the scope of the present invention and testing may be implemented by merely placing the transducer 3 against the part 2 being tested with interposition of a thin wetting film.

The employed measurement principle is based on transmitting an ultrasonic wavetrain E into the part 2 which is then partly reflected (R) inside the part 2 when at a defect 9 in the part 2. The frequency at which consecutive wavetrains are generated is called the measurement repeat frequency. Because the part 2 rotates continuously, its testing as a body of revolution is continuous.

Testing is implemented on consecutive slices by longitudinally displacing the transducer 3 in steps.

Figure 2:
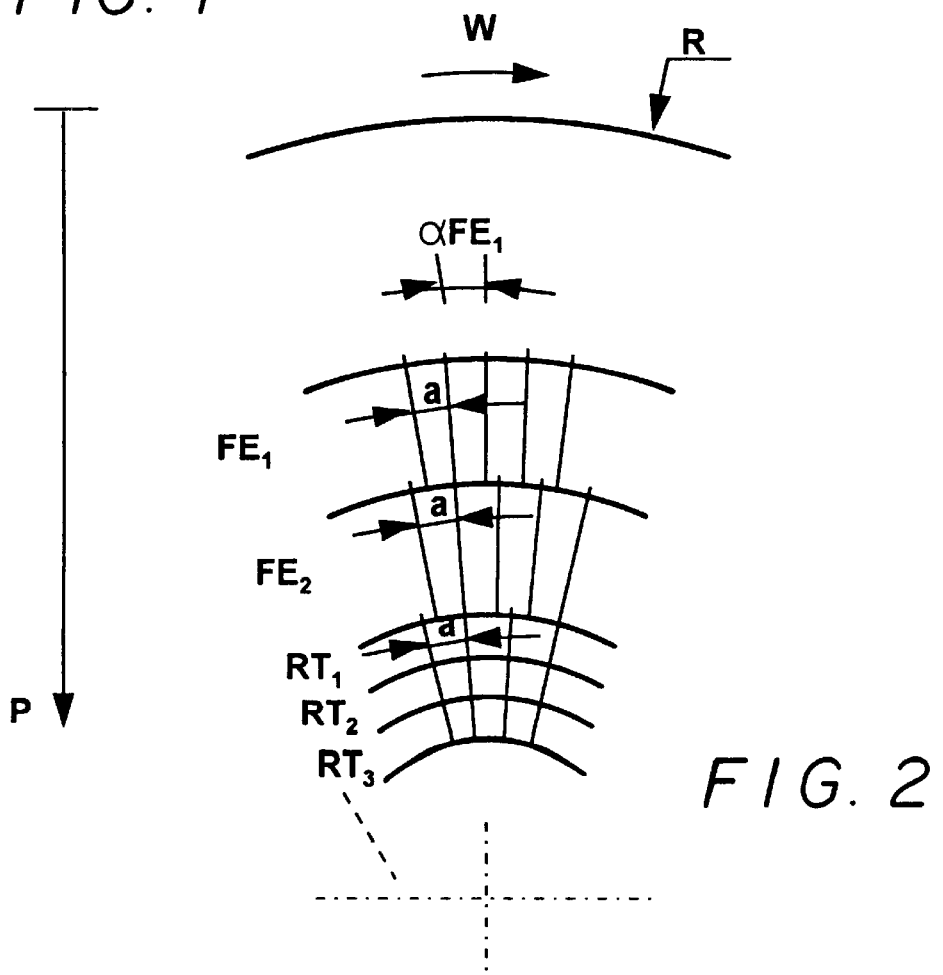
FIG. 2 is a partial cross-section of a billet slice to be tested according to the invention.

FIG. 2 is a partial cross-section of a billet slice being tested.

Each billet slice is divided into annuli located at different depths, each annuli in turn being sub-divided into consecutive and regularly distributed angular sectors. Each annular sector comprises a testing zone. Six annuli are shown in FIG. 2. The first annulus corresponds to a peripheral zone which may be tested in a known manner by one or more compact, single-element transducers each focused at a given depth within the peripheral zone.

The next two annuli correspond to intermediate zones $FE_1$ and $FE_2$ of mean depths $P_1$ and $P_2$, respectively. The last three annuli correspond to the deepest zones $RT_1$, $RT_2$, $RT_3$ of mean depths $P_3$, $P_4$, $P_5$, respectively.

The ultrasonic billet testing method comprises transmitting ultrasonic waves into the part 2, with the focusing being carried out in two different modes which are selected depending on the depth of the zone being tested.

The $FE_1$ and $FE_2$ intermediate zones at depths $P_1$, $P_2$ are tested using an electronic focusing mode. To test the deeper zones $RT_1$, $RT_2$, $RT_3$, a time-reversal focusing mode is used.

In the electronic focusing mode, focusing is carried out by applying predetermined time delays to each piezoelectric pellet of the transducer 3. The transducer 3 is controlled electronically, the time delays being determined prior to testing, for example using modelling software. The time delays may be acquired by calibrating in an autofocus mode, or in a time-reversal mode, with respect to a reference part containing reference defects to determine the optimal delay relationships for use with the particular billet to be tested. The delay relationships also may be amplitude modulated depending on the channels (one channel being associated with one piezoelectric pellet).

The autofocus and time-reversal modes are techniques which utilize auto-focusing on a defect which has an acoustic impedance different from the ambient material. The calibration carried out in an autofocus mode comprises transmitting an unfocused beam of ultrasonic waves toward a test zone of the reference part and determining the maxima of the received echo signals in each channel to infer the time delays linked to the reference defect in that test zone. The delay relationship so defined varies only with the depth of the reference defect and with the depth of field of the focal spot. The same procedure must be carried out on reference defects located at different depths spanning the full thickness of the part to be tested. The set of relationships is stored and used in testing of the part 2.

The calibration carried out in a time-reversal mode comprises several stages. The first stage transmits an unfocused or barely focused beam of ultrasonic waves toward a first test zone of the reference part. The second stage receives first echo signals returned by the reference defect and by the ambient material and, for each piezoelectric pellet, memorizes the shape and time-position of the echo signals, A third stage retransmits these echo signals to the same test zone in inverted time sequence, the last received signal being the first retransmitted signal. The second and third stages may be repeated to amplify the echo signals of the most reflecting reference defect relative to those of the ambient material. The maxima of the echo signals corresponding to the reference defect are then determined and the time delays linked to the reference defect are inferred. Just as in the case of the autofocus mode, the same procedure must be carried out on reference defects located at different depths spanning the full thickness of the part to be tested. The set of relationships so ascertained during the calibration is stored and used in testing of the part 2.

The deepest billet zones are tested entirely in one time-reversal mode. The above described calibration procedure is used on the part 2 by replacing the reference part with the part 2; otherwise, the set of relationships ascertained by calibration with the reference part is used as a first application of the time reversal sequence on the part 2.

Each transmission of ultrasonic waves in the electronic focusing mode or each sequence of three consecutive transmissions in the time reversal mode is focused onto a predetermined billet sector, the focal point being enclosed by a focal spot which is elongated along the axis of propagation of the ultrasonic waves and which is cylindrical at its middle.

Figure 3:
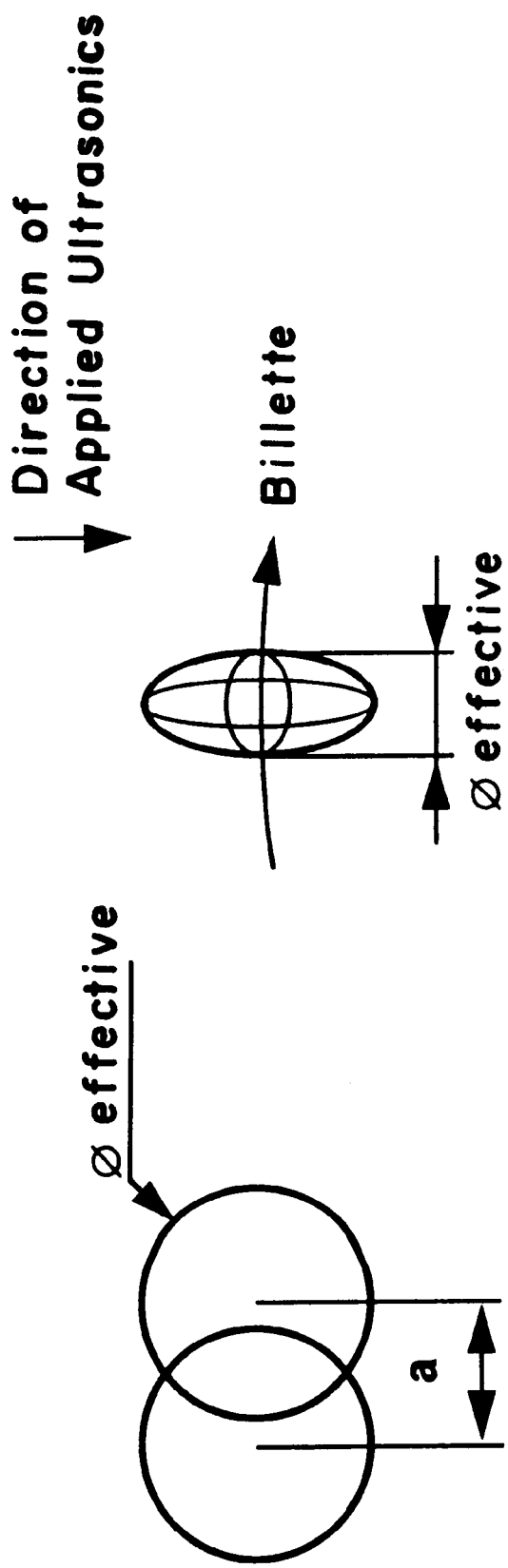
FIG. 3 is an illustrative focal spot inside a part generated by a focusing transducer.

FIG. 3 shows such an illustrative focal spot.

A circumferential forward step of the billet between two adjacent sectors is denoted by "a" and is less than the effective diameter of the focal spot, denoted $\phi_{eff}$ whereby the focal spots from the illumination of two adjacent sectors will overlap transversely. The effective diameter of the focal spot is defined as the largest diameter of the spot in its center cylindrical portion and in a center plane perpendicular to the axis of propagation of the ultrasonic waves.

Illustratively, the forward step may be chosen equal to 70% of the diameter of the focal spot.

In order to maintain the same defect detection sensitivity level throughout the tested volume, the forward step of the billet between two transmissions or between two transmission sequences in two adjacent sectors is approximately constant regardless of the tested depth.

The corresponding angular sector $\alpha_p$ depends on the depth P, namely $\alpha_p = a/2\pi(R-P)$, where R is the billet radius. The angular sector increases as the depth increases, and accordingly the required number of ultrasonic transmissions decreases as the tested depth increases.

Figure 4:
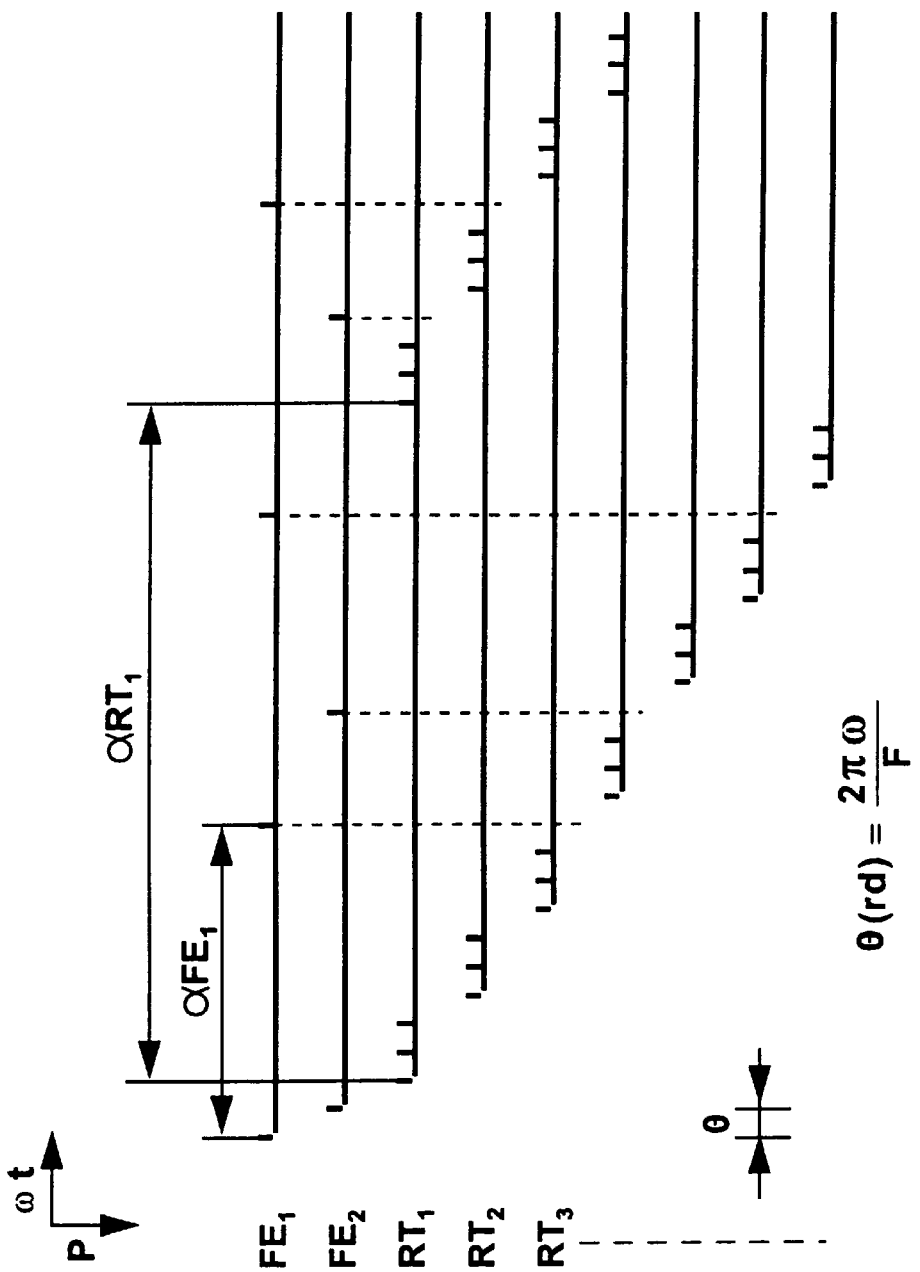
FIG. 4 is an illustrative time plot of ultrasonic transmissions into different zones of a billet slice.

FIG. 4 is an illustrative time plot of the ultrasonic wave transmissions in the different billet zones for one billet slice.

Each billet slice is tested only during one billet revolution. Therefore, all the ultrasonic wave transmissions required to test the volume of a billet slice must have been completed within one revolution.

During one billet rotation, the transmitted waves are focused either by the electronic focusing mode ($FE_1$, $FE_2$) or by the timer reversal mode ($RT_1$, $RT_2$, $RT_3$), depending on the depths of the zones being tested. These two modes are used in an interlacing manner in order to optimally cover the full volume of the billet slice being tested.

This optimization is implemented, on one hand, with due consideration of the need for several consecutive transmissions in the time reversal mode and, on the other hand, by taking into account the circumferential billet advance step between two transmissions or between two consecutive sequences of transmission.

The number of ultrasonic transmissions n in one billet revolution is related to the angular speed ω of the billet and to the repeat frequency F of the directed wave application according to the following equation: $n = [F(Hz)/\omega_{rps}]$, where rps denotes the angular speed measured in revolutions per second.

Because the time reversal mode requires several (usually three) consecutive transmissions, a limit must be placed on the displacement of the tested zone between each transmission. An angular sector θ=(2πω)/F corresponds to this limited displacement.

Figure 5:
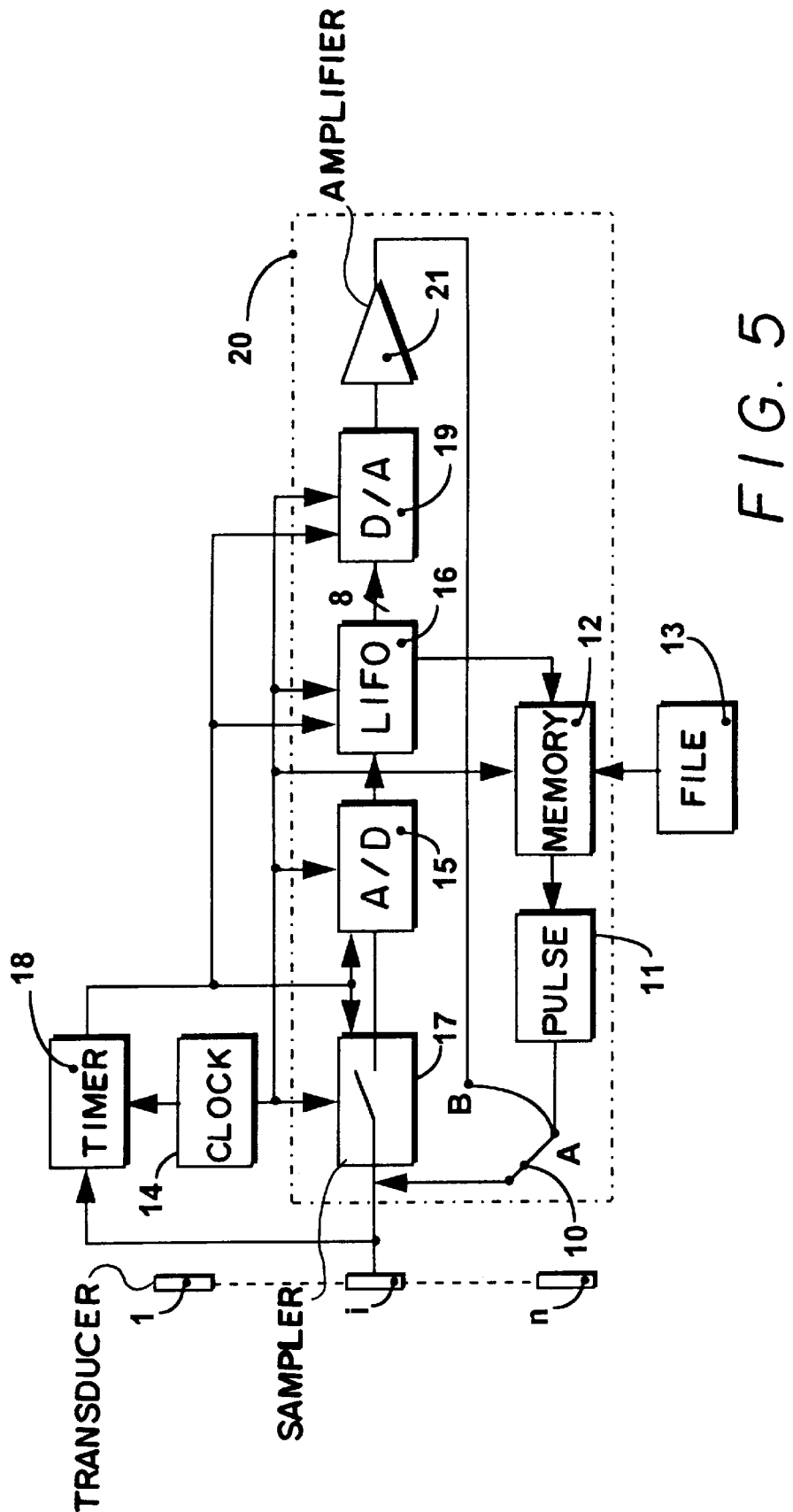
FIG. 5 is a functional block diagram of a processing channel for one element of a multielement transducer with multichannel electronics according to the invention; and, FIG. 6 is an illustrative multielement transducer according to the invention.

FIG. 5 shows a block diagram of a processing channel assigned to a transducer element of order "i" in accordance with the multichannel electronics of the invention.

Each channel comprises a switch 10 for selecting one of two possible operating modes. Position A selects the electronic focusing mode and position B selects the time reversal mode.

In the electronic focusing mode, the transducer element of order "i" receives pulses from a pulse generator 11. A time delay imparted to the transmitted pulses comes from a memory 12 controlled by an internal clock 14. The contents of the memory 12 may be managed in two different ways, depending on whether the delay relationships are determined theoretically by modelling software, in which case the delays are stored in a file 13, or whether the delay relationships are determined by autofocusing on the defects of a reference part, in which case the delays are acquired by calibration and the delays are digitized by an analog/digital converter 15 and stored in a LIFO memory 16.

In the time reversal mode, each channel comprises a sampler 17 to provide analog samples of the echo signal received at the transducer "i" at the frequency of the clock 14 during the timer intervals, set by a timer 18, of duration T long enough so that all transducer elements receive the echo signal. The analog/digital converter 15 follows the sampler 17. In general, 8-bit conversion suffices to satisfactorily render the echo dynamics. The octets representing each sample and are stored in the LIFO memory 16, configured in queue—Last In, First Out—and having sufficient capacity to store all samples received during the time interval T. Time reversal is carried out only over this duration T.

The timer 18 is designed to start the sampling after a predetermined time following energization by the pulse generator 11. The predetermined time is easily estimated when the ultrasonic speed of propagation in the medium is known.

The timer 18 also is designed to trigger the transmission of the reversed echo signal a brief time after receipt of the echo: this time preferably shall be brief (for instance several milliseconds) to preclude modification of the medium or the position of the part 2 during the two-way trip.

To allow transmission of the reversed echo signal, each channel 20 comprises a digital/analog converter 19 followed by a high-gain amplifier 21. The output of the amplifier 21 is applied to the particular transducer "i".

Figure 6:
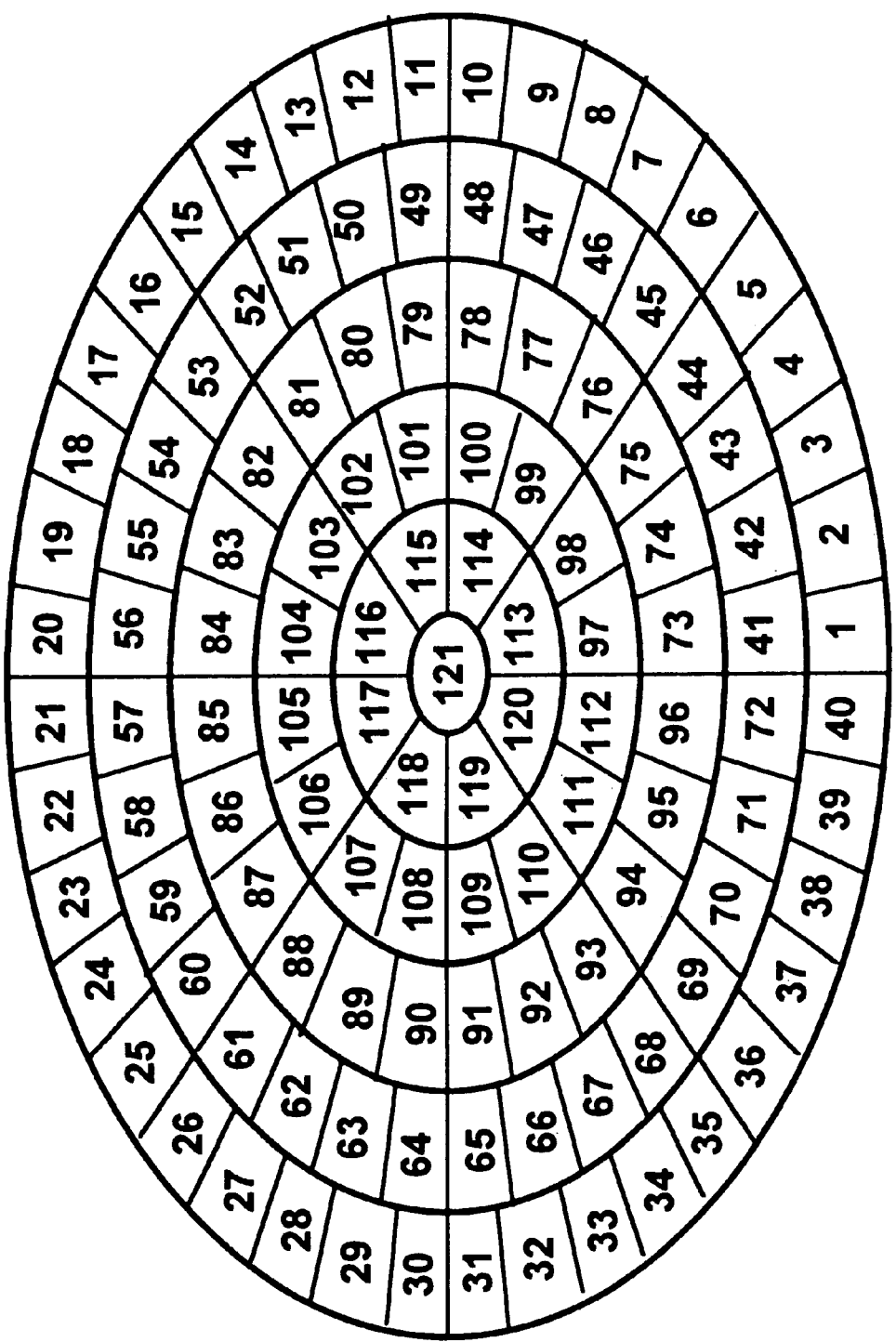

FIG. 6 shows an illustrative embodiment of a multielement transducer according to the invention.

Transducer elements 1 through 121 are piezoelectric pellets configured in a matrix. The matrix configuration is annular and sectorial. The dimensions of the 121 sectors are substantially the same. The transducer is prefabricated to be prefocused in the zone of the core of the billet. Prefocusing is assured by a Fermat surface.

What is claimed is:

1. An ultrasonic testing method for a part of complex geometry which has a volume and a longitudinal axis, the method comprising the steps of:

rotating the part being tested;

transmitting ultrasonic waves with a single multi-element ultrasonic transducer into zones at different depths of the part while the part is rotating;

focusing the ultrasonic waves with said ultrasonic transducer operating in two different focusing modes, namely a time reversal mode and an electronic focusing mode, wherein the focusing method for each particular zone is selected as a function of the depth of the particular zone;

selecting said time reversal focusing mode to test central zones at a core of the part around the longitudinal axis;

selecting said electronic focusing mode to test intermediate zones situated between the central zones and peripheral zones of the part; and, using the time reversal and electronic focusing modes in a time-interlaced, alternating manner to optimally cover the entire volume of the part being tested.

2. The ultrasonic testing method according to claim 1, wherein in the electronic focusing mode, the focusing of the ultrasonic waves comprises:

imparting predetermined time delays to different ultrasonic-wave transmission channels.

3. The ultrasonic testing method according to claim 2, wherein in the electronic focusing mode, the focusing of the ultrasonic waves further comprises:

predetermining the time delays by modelling software.

4. The ultrasonic testing method according to claim 2, wherein in the electronic focusing mode, the focusing of the ultrasonic waves further comprises:

predetermining the time delays by autofocusing calibration of a reference part which includes reference defects located at different depths therein.

5. The ultrasonic testing method according to claim 4, wherein the autofocusing calibration comprises the steps of:

transmitting an unfocused beam of ultrasonic waves toward a zone of the reference part;

receiving echoes reflected by the reference defects; detecting maxima of the received echoes and time delays associated with the maxima of the received echoes; and, storing the time delays associated with the maxima.

6. The ultrasonic testing method according to claim 4, wherein the autofocusing calibration comprises a time reversal focusing procedure carried out on the reference part which requires several transceiving iterations of ultrasonic waves for each zone.

7. The ultrasonic testing method according to claim 1, further comprising the step of:

testing the part in consecutive slices, each slice being divided into annuli and each annulus being subdivided into angular sectors, each angular sector constituting one of the zones.

8. The ultrasonic testing method according to claim 7, further comprising the step of:

testing each slice during one revolution of the part.

9. The ultrasonic testing method according to claim 7, further comprising the step of:

testing two consecutive sectors by circumferentially displacing the part by one predetermined, and approximately constant, advance step regardless of the depth of the zone.

* * * * *